US00PP29474P3

(12) United States Plant Patent
Wood

(10) Patent No.: US PP29,474 P3
(45) Date of Patent: Jul. 10, 2018

(54) ***GREVILLEA* PLANT NAMED 'TWD02'**

(50) Latin Name: *Grevillea laurifolia*
Varietal Denomination: TWD02

(71) Applicant: Michael Wood, Bega (AU)

(72) Inventor: Michael Wood, Bega (AU)

( * ) Notice: Subject to any disclaimer, the term of this patent is extended or adjusted under 35 U.S.C. 154(b) by 0 days.

(21) Appl. No.: 15/731,219

(22) Filed: May 4, 2017

(65) Prior Publication Data

US 2017/0325377 P1 Nov. 9, 2017

(30) Foreign Application Priority Data

May 4, 2016 (AU) ..... PBR 2016/100

(51) Int. Cl.
*A01H 5/00* (2018.01)
*A01H 5/02* (2018.01)

(52) U.S. Cl.
USPC ..... Plt./226
CPC ..... *A01H 5/02* (2013.01)

(58) Field of Classification Search
USPC ..... Plt./226
See application file for complete search history.

*Primary Examiner* — Susan McCormick Ewoldt
(74) *Attorney, Agent, or Firm* — Samuel R. McCoy, Jr.

(57) ABSTRACT

A new and distinct *Grevillea laurifolia* cultivar named 'TWD02' which is characterized by a very prostrate growth habit with a vigorous growth rate, dark green mature foliage and bronze colored juvenile foliage with red immature branches, dense foliage, racemose inflorescence with approximately 40 dark red-purple florets with prominent bright red-purple exserted styles, and the stability of these characteristics from generation to generation.

2 Drawing Sheets

Latin name of the genus and species: The Latin name of the genus and species of the novel variety disclosed herein is *Grevillea laurifolia.*

Variety denomination: The inventive variety of *Grevillea laurifolia* disclosed herein has been given the variety denomination 'TWD02'.

CROSS REFERENCE TO RELATED APPLICATIONS

This application claims priority to the Australian Plant Breeder's Rights application number 2016/100, filed on May 4 2016, which is herein incorporated by reference.

BACKGROUND OF THE INVENTION

Parentage: In January of 2009, a unique *Grevillea* seedling was discovered by the inventor at his commercial nursery in Kalaru, New South Wales, Australia. The seedling was found growing in a cultivated crop of *Grevillea laurifolia* (unnamed common form of the species); the claimed plant exhibited a faster rate of growth compared to all other surrounding plants, which is known to grow slowly. The new seedling was isolated and grown to a mature size to confirm the distinctness and stability of the characteristics initially observed. After further evaluation and confirmation of the desirable traits, the claimed plant was selected for commercialization and given the breeder denomination, 'TWD02'.

Asexual Reproduction: 'TWD02' was first asexually reproduced by way of softwood stem cuttings in 2010 at the inventor's nursery in Kalaru, New South Wales, Australia. It was found to grow uniform and reproduce in a stable manner and 10 successive cycles of vegetative propagation have proven to be true to type also.

SUMMARY OF THE INVENTION

The following characteristics have been repeatedly observed and represent the distinguishing characteristics of the new *Grevillea* cultivar 'TWD02'. These traits, in combination, distinguish 'TWD02' as a new and distinct cultivar.

1. *Grevillea laurifolia* 'TWD02' exhibits a short plant height and a prostrate, densely foliaged growth habit; and
2. *Grevillea laurifolia* 'TWD02' exhibits a fast rate of growth; and
3. *Grevillea laurifolia* 'TWD02' exhibits dark green mature foliage and bronze colored juvenile foliage, with red immature branches; and
4. *Grevillea laurifolia* 'TWD02' exhibits a secund raceme inflorescence with approximately 40 dark red-purple florets with prominent bright red-purple exserted styles.

BOTANICAL DESCRIPTION OF THE PLANT

Figure 1:
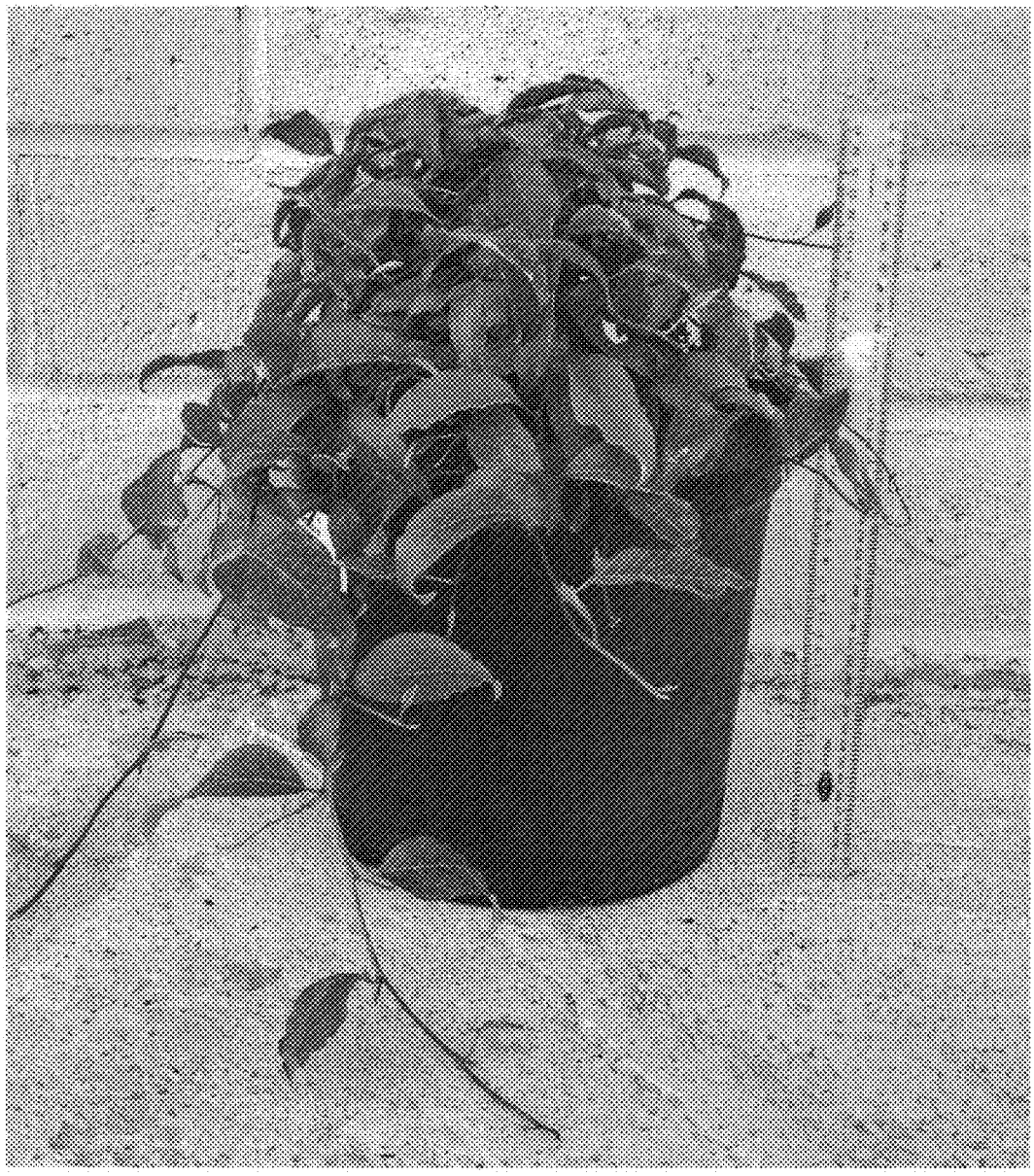
FIG. 1 illustrates, as nearly true as it is reasonably possible to make the same in color photographs of this type, an exemplary 1.5 year old 'TWD02' plant grown outdoors in Clarendon, New South Wales, Australia.
Figure 2:
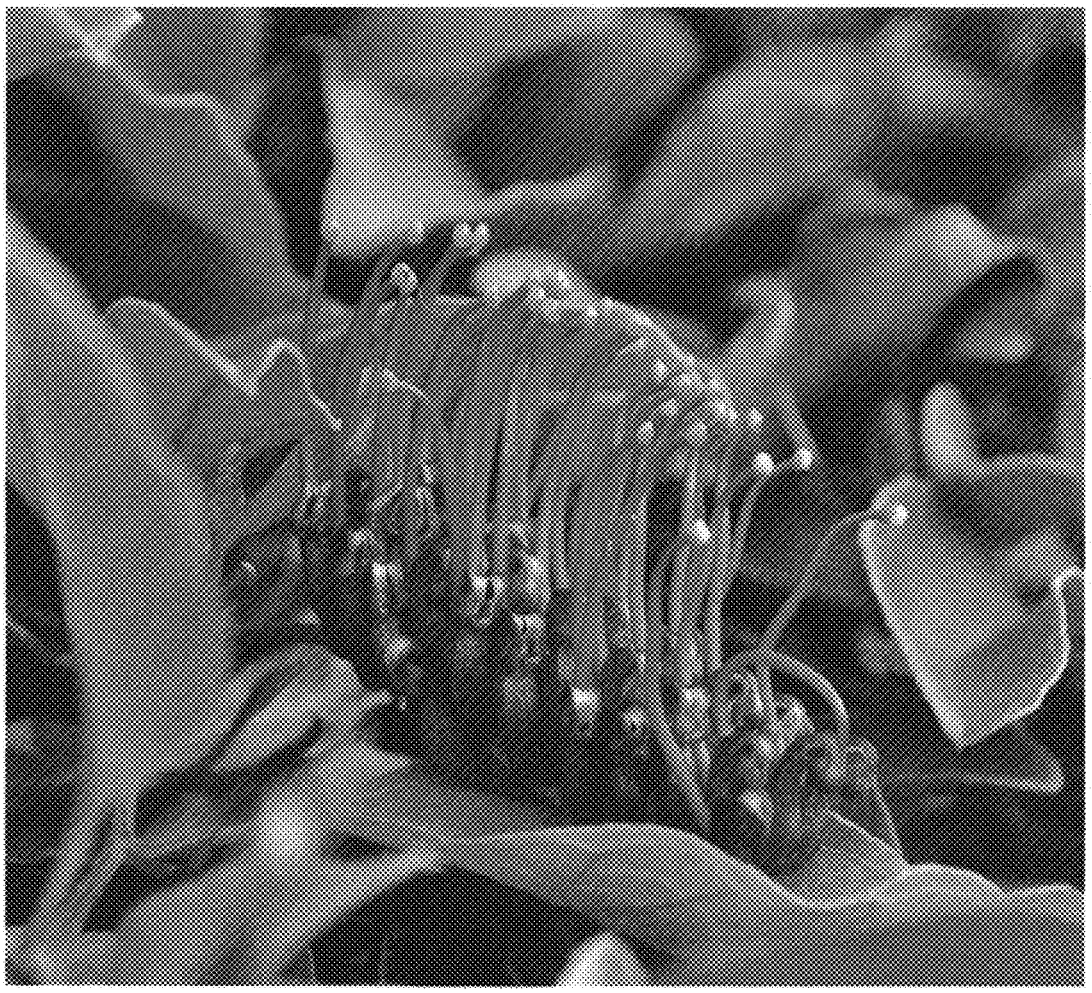
FIG. 2 illustrates, as nearly true as it is reasonably possible to make the same in color photographs of this type, an exemplary inflorescence of the claimed plant.

The following is a detailed botanical description of a new and distinct variety of a *Grevillea laurifolia* ornamental plant known as 'TWD02'. Plant observations were made on plants grown in Clarendon, New South Wales, Australia. Unless indicated otherwise, the descriptions disclosed herein are based upon observations made from 1.5 year-old mature 'TWD02' plants, grown in a 30 cm nursery pot. These plants were grown outdoors in full sun. Plants were not fertilized and were periodically watered with overhead irrigation, as needed. No pest and disease measures were taken. Observation data was recorded in the April of 2017.

Those skilled in the art will appreciate that certain characteristics will vary with older or, conversely, younger plants. 'TWD02' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'TWD02' and comparisons with the presumed parents are provided below.

General plant description:

*Plant habit.*—Prostrate; flat and spreading.

*Height.*—Approximately 35 cm.

*Width.*—Approximately 300 cm.

*Hardiness.*—USDA Zone 10 to 11.

*Environmental tolerances.*—'TWD02' has not yet been observed under all conditions but has shown to be heat tolerant, adapting well to temperatures of 112 degrees Fahrenheit without any noticeable damage. 'TWD02' has shown good drought tolerance, typical of the species, once established.

*Pest and disease susceptibility or resistance.*—Neither susceptibility nor resistance to common pests and diseases known to affect *Grevillea* have been observed.

*Propagation.*—Propagation is accomplished using softwood cuttings.

*Time to develop roots.*—8 to 12 weeks.

*Crop time.*—Approximately 6 months are needed to produce a fully rooted cutting; approximately 12 months are needed to produce a marketable plant in a 1 gallon nursery pot.

Root system:

*Branching habit.*—A network of large primary roots, giving rise to a plurality of fibrous roots; densely rooted.

*Distribution of roots in the soil profile.*—Evenly distributed from shallow to deep.

*Texture.*—Mature roots are smooth; juvenile roots are fleshy.

*Color.*—Mature roots are greyed-orange, nearest to in between RHS 166B and 175C; juvenile roots are greyed-orange, nearest to RHS 164D.

Stems:

*Branching habit.*—Single main stem which freely branches; numerous prostrate to decumbent secondary branches.

*Main stem.*—Attitude — Erect; nearly 90 degrees to horizontal. Cross section — Rounded. Dimensions — Approximately 100 mm long and 60 mm in diameter. Color — Greyed-orange, RHS 177A with fissures colored greyed-green, RHS 197C.

Texture — Smooth.

*Lateral branches.*—Aspect — At nearly 90 degrees from main stem. Cross section — Rounded. Strength — Medium. Length of lateral branches — Can grow up to 300 cm. Diameter of lateral branches — Ranging from 8 to 12 mm at the base, depending on age of the branch. Internode length on lateral branches — 35 mm on average. Texture of lateral branches — Strigose. Color, juvenile — Yellow-green, RHS 145B, and becoming heavily suffused with greyed-red, in between RHS 181B and 181C, towards the distal portion of the branch; the most juvenile portion of the branch is entirely greyed-red, in between RHS 181B and 181C. Color, mature — Greyed-orange, RHS 177A with fissures colored greyed-green, RHS 197C.

Foliage:

*Arrangement.*—Alternate.

*Attachment.*—Petiolate.

*Division.*—Simple.

*Shape.*—Elliptic.

*Length.*—100 to 120 mm.

*Width.*—25 to 30 mm.

*Thickness.*—0.2 mm.

*Apex.*—Acuminate.

*Base.*—Cuneate.

*Margin.*—Entire and lightly undulated.

*Texture, adaxial surface.*—Strigose.

*Texture, abaxial surface.*—Strigose.

*Color.*—Juvenile foliage, adaxial surface — Greyed-orange, RHS 172C; occasionally greyed-red, RHS 178B. Juvenile foliage, abaxial surface — Yellow-green, RHS 145A, and heavily suffused with greyed-orange, nearest to a combination of RHS 166B and 166C. Mature foliage, adaxial surface — Yellow-green, RHS 144A, and very lightly suffused with greyed-orange, RHS 166B. Mature foliage, abaxial surface — Yellow-green, RHS 145A.

*Venation.*—Pattern — Cross venulate. Vein color, adaxial surface — Yellow-green, RHS 145B, and lightly suffused with greyed-red, in between RHS 181B and 181C, towards the base. Vein color, abaxial surface — Yellow-green, RHS 145B, and lightly suffused with greyed-red, in between RHS 181B and 181C, towards the base.

*Petiole.*—Dimensions — 15 to 17 mm long and 1.5 to 2 mm in diameter. Color — Yellow-green, RHS 145B, and suffused with greyed-red, in between RHS 181B and 181C. Texture — Strigose.

*Stipule.*—Arrangement — Free. Shape — Elongated. Apex — Acute. Dimensions — 7 mm long and 2 mm wide. Color — Greyed-red, in between RHS 181B and 181C. Texture — Strigose.

Inflorescence:

*Type.*—Terminal and axillary racemes with clusters of approximately 40 flowers.

*Natural flowering season.*—Spring to summer in the southern hemisphere.

*Dimensions.*—Dimensions vary but a mature terminal raceme is up to 70 mm in length, from the base of the peduncle to the stigma of the terminal-most flower, and approximately 50 mm wide, from style to style of the most outstretched lateral flowers.

*Quantity.*—Moderately floriferous.

*Peduncle.*—Dimensions — 30 to 35 mm long and 1.5 mm wide. Attitude — Approximately 30 degrees from horizontal. Color — Greyed-red, in between RHS 181B and 181C. Texture — Strigose. Strength — Strong.

Bud:

*Dimensions.*—9 mm long and 3 mm in diameter.

*Shape.*—Narrowly oblong and clubbed at the distal end.

*Color.*—Red-purple, RHS 59B.

*Pubescence.*—Finely pubescent.

Flower:

*Pedicels.*—Dimensions — 3 to 4 mm long and 1.0 mm wide. Color — Red-purple, RHS 59C. Texture and pubescence — Strigose. Strength — Strong.

*Perianth.*—General description — Small, pedicellate floret with a closed perianth which creates a floral tube made up of two dorsal and two ventral tepals, which terminate at their apex and form a ball-like "tepal limb" which house the anthers. Quantity of flowers — Approximately 40 flowers per inflorescence. Sequence and rate of opening — Racemose; sequential proximal to distal, moderate around 5 days from first to last on each inflorescence. Persistence — Not persistent. Fragrance — Not fragrant. Aspect — Erect. Tepals — Quantity — 4 fused tepals. Arrangement — Fused into a tube. Dimensions — Perianth tube width is approximately 3 mm, with an average length of 12.5 mm. Texture, pubescence and luster — Smooth, pubescent with fine, silky hairs, and matte luster. Color when opening — Red-purple, RHS 59C. Color when fully opened — Red-purple, RHS 59C. Petal color fading to — Not fading.

Reproductive organs:

*Stamens.*—Quantity — Four. Attachment — Adnate to the perianth tube. Anthers — Shape — Irregularly triangular. Diameter — 1 mm. Color — Yellow, nearest to RHS 11C. Pollen — Low to medium. Pollen Color — White, nearest to RHS 155C.

*Pistils.*—Quantity — One. Dimensions — Approximately 30 mm long and 1.5 mm wide. Stigma — Shape — Club-like. Dimensions — 2 mm long and 2.5 mm wide. Color — Yellow-green, RHS 145A. Texture — Smooth. Style — Dimensions — 28 mm long and 1.5 mm wide. Color — Red-purple, nearest to RHS 58B. Texture — Smooth. Ovary — Position — Superior. Dimensions — 15 mm long and 10 mm wide. Texture and pubescence — Smooth.

Seed:

*Quantity.*—One.

*Shape.*—Ovoid with a thin papery wing that is approximately 1 mm wide.

*Color.*—Brown, RHS 200A.

*Dimensions.*—9 mm long and 5 mm in diameter.

COMPARISONS WITH THE PRESUMED PARENTS AND CLOSEST KNOWN VARIETY

'TWD02' may be distinguished from the parent *Grevillea laurifolia* (unnamed common form of the species) by the characteristics described in Table 1.

TABLE 1

| Characteristic | 'TWD02' | *Grevillea laurifolia* |
|---|---|---|
| Foliage density. | Low to medium. | Medium to high. |
| Quantity of inflorescence. | Low. | Medium to high. |

'TWD02' may be distinguished from *Grevillea laurifolia* 'Blue Mountain Rambler' (unpatented) by the characteristics described in Table 2.

TABLE 2

| Characteristic | 'TWD02' | 'Blue Mountain Rambler' |
|---|---|---|
| General coloration of mature foliage. | Dark green. | Lighter green. |
| Plant vigor. | Low to medium. | High. |

That which is claimed is:

1. A new and distinct variety of *Grevillea laurifolia* plant named 'TWD02', substantially as described and illustrated herein.

* * * * *